(12) United States Patent
Sideris

(10) Patent No.: US 7,497,934 B2
(45) Date of Patent: Mar. 3, 2009

(54) SYSTEM AND METHOD

(75) Inventor: Dimitrios Sideris, London (GB)

(73) Assignee: Deltadot Ltd., London (GB)

( * ) Notice: Subject to any disclaimer, the term of this patent is extended or adjusted under 35 U.S.C. 154(b) by 682 days.

(21) Appl. No.: 10/344,290

(22) PCT Filed: Jul. 20, 2001

(86) PCT No.: PCT/GB01/03281

§ 371 (c)(1), (2), (4) Date: Jun. 19, 2003

(87) PCT Pub. No.: WO02/12877

PCT Pub. Date: Feb. 14, 2002

(65) Prior Publication Data

US 2004/0013567 A1  Jan. 22, 2004

(51) Int. Cl.
*G01N 27/447* (2006.01)
*G01N 27/453* (2006.01)
*G01N 33/50* (2006.01)
*G01N 30/02* (2006.01)

(52) U.S. Cl. ................... 204/452; 204/603; 204/612; 204/461; 422/70; 702/19; 702/22

(58) Field of Classification Search ............... 204/450, 204/600, 603, 612, 461, 452; 422/70; 702/19–22, 702/142; 73/1.37
See application file for complete search history.

(56) References Cited

U.S. PATENT DOCUMENTS 5,114,551 A    5/1992    Hjerten et al.

(Continued)

FOREIGN PATENT DOCUMENTS

GB    2 259 980    3/1993

(Continued)

OTHER PUBLICATIONS

International Search Report for International Application No. PCT/GB01/03281 filed Jul. 20, 2001, mailed May 27, 2002.

(Continued)

*Primary Examiner*—Alex Noguerola
(74) *Attorney, Agent, or Firm*—Ungaretti & Harris LLP

(57) ABSTRACT

An analysis system for and method of enabling determination of the velocities of migrating objects and also classifying migrating objects into groups having a common constraint. In one aspect the present invention provides an analysis system for and method of enabling determination of the velocities of migrating objects, the system comprising: a space-time map generator for generating a space-time map of points representative of the signal peaks of signals detected at a plurality of spaced positions; and a vertex finder for identifying at least one vertex from the space-time map, with a single vertex being identified for each group of objects having a common constraint and the velocities of the objects being determinable from the sets of points in the space-time map corresponding to the respective objects as fitted to the respective vertex. In another aspect the present invention provides an analysis system for classifying migrating objects into groups each having a common constraint, the system comprising: a space-time map generator for generating a space-time map of points representative of the signal peaks of signals detected at a plurality of spaced positions; and a vertex finder for identifying at least one vertex from the space-time map, with a single vertex being identified for each group of objects having a common constraint.

52 Claims, 3 Drawing Sheets

U.S. PATENT DOCUMENTS

| | | | |
|---|---|---|---|
| 5,141,609 A | 8/1992 | Sweedler et al. | |
| 5,627,643 A | 5/1997 | Birnbaum et al. | |
| 6,017,435 A | 1/2000 | Hassard et al. | |
| 6,103,533 A | 8/2000 | Hassard et al. | |

FOREIGN PATENT DOCUMENTS

| | | |
|---|---|---|
| WO | WO-96/35946 | 11/1996 |
| WO | WO-98/45948 | 10/1998 |
| WO | WO-98/49548 | 11/1998 |

OTHER PUBLICATIONS

Neumann, M. et al. "Capillary Array Scanner For Time-Resolved Detection and Identification of Fluorescently Labelled DNA Fragments," Journal of Chromatography A, Feb. 25, 2000, vol. 871, No. 1-2 pp. 299-310.

Alward M.R., "Trends in DNA Genotyping," Trends in Analytical Chemistry, May 1, 1997, vol. 16, No. 5, p. IX.

Lu, S.X. et al., "Side-Entry Excitation and Detection of Square Capillary Array Electrophoresis for DNA Sequencing," Journal of Chromatography A, Aug. 20, 1999, vol. 853, No. 1-2, pp. 359-369.

SYSTEM AND METHOD

This Application is a continuation of International Application No. PCT/GB01/03281, with an international filing date of 20 Jul. 2001, now pending, claiming priority from Great Britain Application No. GB00/19496.9, filed 08 Aug. 2000, now pending, and herein incorporated by reference.

DESCRIPTION

Technical Field

The present invention relates to an analysis system for and method of determining the velocities of migrating objects, such as sample components travelling through a channel, and also to an analysis system for and method of classifying migrating objects into groups each having a common constraint, such as the components in a plurality of separately-provided sample plugs. In particular, but not exclusively, the present invention finds application in relation to electrophoretic measurements. The technique of the present invention is the EVA™ analysis technique.

BACKGROUND OF THE INVENTION

Electrophoretic separation techniques are separation techniques in which the components of sample plugs are separated in a separation column by the differences in the migration rates of those sample components on the application of an electric field therealong, where absorption, fluoroescence, electrochemistry, conductivity, radioactivity and mass spectrometry can be all used to detect the electrophoretic separation.

As will be appreciated, the ability to determine accurately the velocities of migrating components, such as components electrophoretically separated in a separation column, is highly desirable. In this regard, the present inventor has identified that the velocities of the migrating components provided in a single sample plug have a common vertex to which the points in space-time co-ordinates can be fitted, and hence allow for improved resolution of the velocities.

Also, the ability to classify migrating objects into groups each having a common constraint, either time or spatially related, has particular application in allowing migrating components to be detected in a single detection sequence and identified as being from one of a plurality of separately-provided multi-component sample plugs. Whilst this technique has application in very many fields, one particular application is the sequencing of polymeric samples, such as DNA samples, where sample plugs provided separately, either in space or time, and comprising DNA bands having the different base pair terminations can be driven in a single step through a separation channel and yet classified into groups according to the respective sample plug. In this way, sequencing of a polymeric sample, exemplified as a DNA sample, is possible from knowledge of the base pair termination of each sample plug to which the migrating components are assigned and calculation of the length of the DNA bands from the measured velocities. One particular advantage of this technique is that the sample components do not need to be labelled, although labelling could assist in providing for improved detection of the migrating components.

It is thus an aim of the present invention to provide an improved analysis system for and method of determining the velocities of migrating objects, such as sample components travelling through a channel, and also to provide an analysis system for and method of classifying migrating objects into groups each having a common constraint, such as the components in a plurality of separately-provided sample plugs.

SUMMARY OF THE INVENTION

Accordingly, the present invention provides an analysis system for enabling determination of the velocities of migrating objects, comprising: a space-time map generator for generating a space-time map of points representative of the signal peaks of signals detected at a plurality of spaced positions; and a vertex finder for identifying at least one vertex from the space-time map, with a single vertex being identified for each group of objects having a common constraint and the velocities of the objects being determinable from the sets of points in the space-time map corresponding to the respective objects as fitted to the respective vertex.

Preferably, the system further comprises a velocity sorter for determining the nominal velocities associated with the signal peaks in the signals and grouping those signal peaks into sets according to nominal velocity.

Preferably, the space-time map generator is configured to utilise a corrected time component in generating the space-time map according to a function of the electric current variation.

More preferably, the correction is according to the function $t_c = \int I_0/I(t')dt'$ in the range of 0 to t, where t is the measured time, $t_c$ is the corrected time, I is the measured current and $I_0$ is the reference current.

Preferably, the space-time map generator is an equiphase space-time map generator for generating an equiphase space-time map of equiphase points.

More preferably, the equiphase space-time map generator is configured to transform each data set into a set of local slopes and determine the local minima as the minimum absolute local derivatives.

In one embodiment the objects are non-labelled objects.
In another embodiment the objects are labelled objects.
Preferably, the objects are migrated through a channel.
More preferably, the channel comprises a separation channel through which the objects are electrophoretically driven.

In one embodiment the objects comprise components from one sample.

In another embodiment the objects comprise components from a plurality of separate samples.

Preferably, the objects comprise molecular components.
Preferably, the objects comprise polymeric components.
More preferably, the components comprise DNA bands.

The present invention also extends to an electrophoresis apparatus including the above-described system.

The present invention also provides a method of enabling determination of the velocities of migrating objects, comprising the steps of: generating a space-time map of points representative of the signal peaks of signals detected at a plurality of spaced positions; and identifying at least one vertex from the space-time map, with a single vertex being identified for each group of objects having a common constraint and the velocities of the objects being determinable from the sets of points in the space-time map corresponding to the respective objects as fitted to the respective vertex.

Preferably, the method further comprises the steps of determining the nominal velocities associated with the signal peaks in the signals and grouping those signal peaks into sets according to nominal velocity.

Preferably, a time component corrected according to a function of the electric current variation is utilised in generating the space-time map.

More preferably, the correction is according to the function $t_c = \int I_0/I(t')dt'$ in the range of 0 to t, where t is the measured time, $t_c$ is the corrected time, I is the measured current and $I_0$ is the reference current.

Preferably, the space-time map is an equiphase space-time map of equiphase points.

More preferably, the equiphase points are determined by transforming each data set into a set of local slopes and determining the local minima as the minimum absolute local derivatives.

In one embodiment the objects are non-labelled objects.

In another embodiment the objects are labelled objects.

Preferably, the objects are migrated through a channel.

More preferably, the channel comprises a separation channel through which the objects are electrophoretically driven.

In one embodiment the objects comprise components from one sample.

In another embodiment the objects comprise components from a plurality of separate samples.

Preferably, the objects comprise molecular components.

Preferably, the objects comprise polymeric components.

More preferably, the components comprise DNA bands.

The present invention further provides an analysis system for classifying migrating objects into groups each having a common constraint, comprising: a space-time map generator for generating a space-time map of points representative of the signal peaks of signals detected at a plurality of spaced positions; and a vertex finder for identifying at least one vertex from the space-time map, with a single vertex being identified for each group of objects having a common constraint.

Preferably, the system further comprises a velocity sorter for determining the nominal velocities associated with the signal peaks in the signals and grouping those signal peaks into sets according to nominal velocity.

Preferably, the space-time map generator is configured to utilise a corrected time component in generating the space-time map according to a function of the electric current variation.

More preferably, the correction is according to the function $t_c = \int I_0/I(t')dt'$ in the range of 0 to t, where t is the measured time, $t_c$ is the corrected time, I is the measured current and $I_0$ is the reference current.

Preferably, the space-time map generator is an equiphase space-time map generator for generating an equiphase space-time map of equiphase points.

More preferably, the equiphase space-time map generator is configured to transform each data set into a set of local slopes and determine the local minima as the minimum absolute local derivatives.

In one embodiment the objects are non-labelled objects.

In another embodiment the objects are labelled objects.

Preferably, the objects are migrated through a channel.

More preferably, the channel comprises a separation channel through which the objects are electrophoretically driven.

Preferably, the velocities of the objects are determinable from the points in the space-time map as fitted to the respective vertex Preferably, the objects comprise molecular components.

Preferably, the objects comprise polymeric components.

More preferably, the components comprise DNA bands.

The present invention also extends to an electrophoresis apparatus including the above-described system.

The present invention yet further provides a method of classifying migrating objects into groups each having a common constraint, comprising the steps of: generating a space-time map of points representative of the signal peaks of signals detected at a plurality of spaced positions; and identifying at least one vertex from the space-time map, with a single vertex being identified for each group of objects having a common constraint.

Preferably, the method further comprises the steps of determining the nominal velocities associated with the signal peaks in the signals and grouping those signal peaks into sets according to nominal velocity.

Preferably, a time component corrected according to a function of the electric current variation is utilised in generating the space-time map.

More preferably, the correction is according to the function $t_c = \int I_0/I(t')dt'$ in the range of 0 to t, where t is the measured time, $t_c$ is the corrected time, I is the measured current and $I_0$ is the reference current.

Preferably, the space-time map is an equiphase space-time map of equiphase points.

More preferably, the equiphase points are determined by transforming each data set into a set of local slopes and determining the local minima as the minimum absolute local derivatives.

In one embodiment the objects are non-labelled objects.

In another embodiment the objects are labelled objects.

Preferably, the objects are migrated through a channel.

More preferably, the channel comprises a separation channel through which the objects are electrophoretically driven.

Preferably, the velocities of the objects are determinable from the points in the space-time map as fitted to the respective vertex.

Preferably, the objects comprise molecular components.

Preferably, the objects comprise polymeric components.

More preferably, the components comprise DNA bands.

BRIEF DESCRIPTION OF THE DRAWINGS

A preferred embodiment of the present invention will now be described hereinbelow by way of example only with reference to the accompanying drawings, in which.

DETAILED DESCRIPTION OF THE PREFERRED EMBODIMENT

Figure 1:
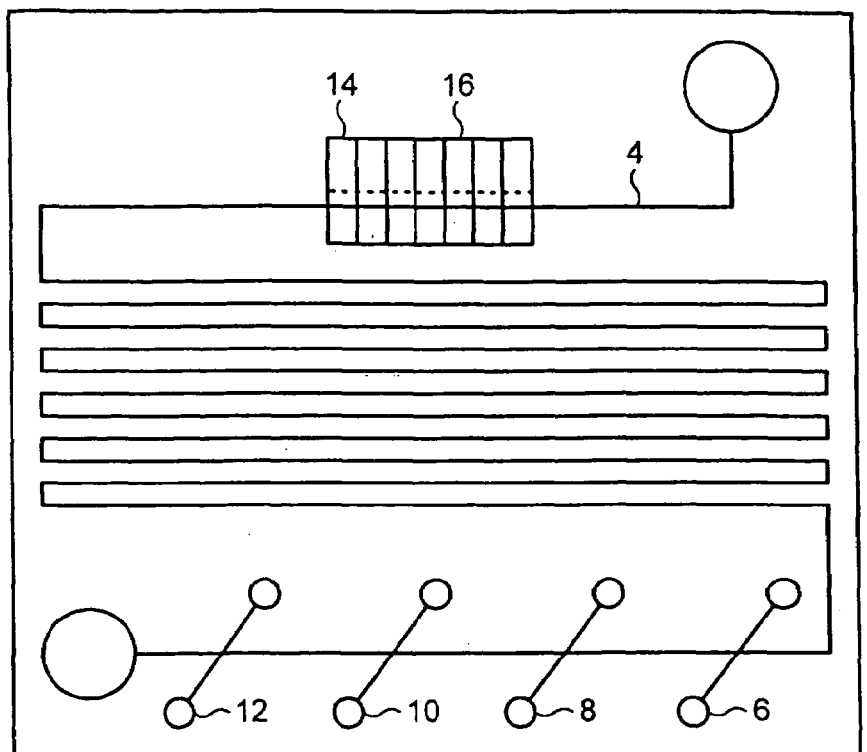
FIG. 1 illustrates the detector chip of an electrophoresis apparatus in accordance with a preferred embodiment of the present invention.
Figure 2:
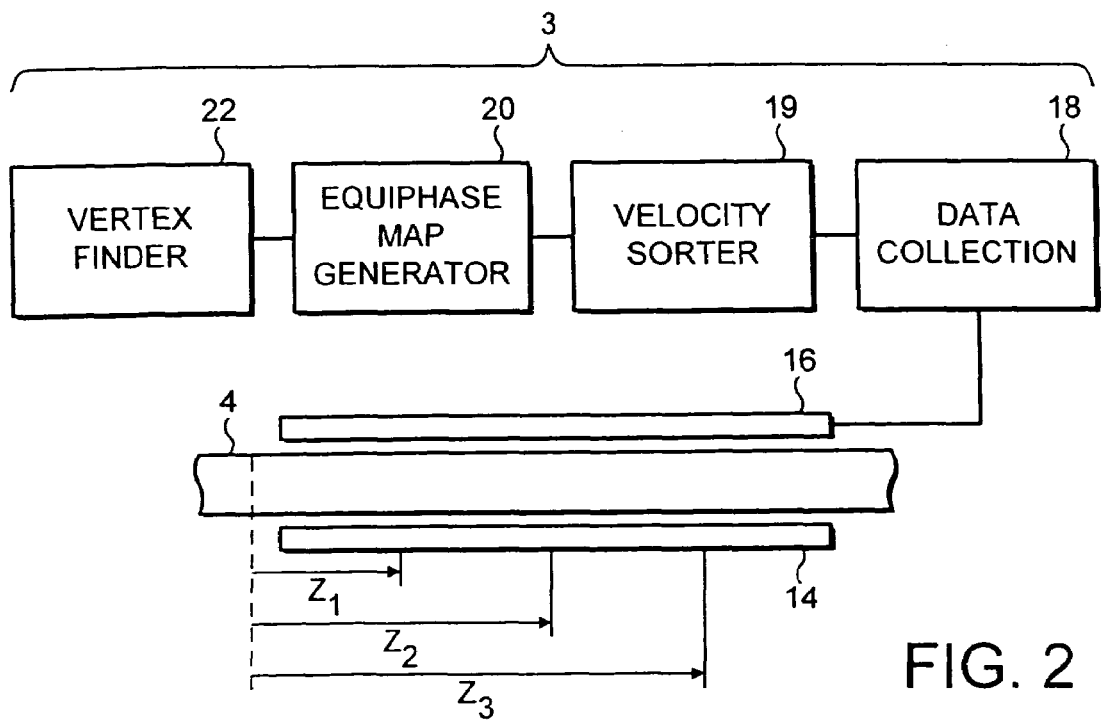
FIG. 2 illustrates the analysis system of the apparatus of FIG. 1.

FIGS. 1 and 2 illustrate an electrophoresis apparatus in accordance with a preferred embodiment of the present invention.

The electrophoresis apparatus includes a detector chip 2 as microfabricated in a substrate chip, and an analysis system 3 for analysing the detection signals generated by the detector chip 2.

The detector chip 2 includes a separation channel 4, in this embodiment a meandering, gel-filled channel, through which the components of one or more sample plugs are in use driven by an applied electrophoretic voltage. The separation channel 4 has a length sufficient to allow separation of the components of the sample plugs. Preferably, the separation channel 4 has a width of from 25 to 100 μm and a length of from 20 to 300 mm. The separation channel 4 includes a plurality, in this embodiment first to fourth, spaced sample-injection ports 6, 8, 10, 12 through which sample plugs including a plurality of components, in this embodiment DNA bands having the respective base pair terminations A, T, G and C, are separately injected into the separation channel 4.

The detector chip 2 further includes a light source 14, in this embodiment a UV light source, disposed along a length of one side of the separation channel 4, and a detector 16 disposed along the length of the other side of the separation channel 4 to detect light transmitted through the separation channel 4, with the presence of the migrating components being detected by the change in the detected light intensity as caused by absorbtion of the incident light. By detecting the sample components in this manner, the sample components need not necessarily be labelled. In this embodiment the detector 16 comprises a pixel detector array (PDA) which includes a plurality of pixels providing detecting elements for detecting the transmitted light at a plurality of positions $z_1$, $z_2$, $z_3$ spaced along the length of the separation channel 4 and outputting a plurality of signals $S_1$, $S_2$, $S_3$. For ease of description, the detector 16 is illustrated as including three detecting elements at three positions $z_1$, $z_2$, $z_3$. It will, however, be understood that in practice the detector 16 comprises a plurality of detecting elements at a plurality of positions $z_1$, $z_2$, $z_3$, ..., $Z_n$, which each output a signal $S_1$, $S_2$, $S_3$, ..., $S_n$. In an alternative embodiment the detector 16 could be provided by a plurality of separate detectors each providing a detecting element. In another alternative embodiment labelled sample components could be used, such as sample components including fluorescent or radioactive labels, which labels would be detected by the detector 16.

The analysis system 3 comprises a data collector 18 for receiving the signals $S_1$, $S_2$, $S_3$ generated by the detector 16 and storing those signals $S_1$, $S_2$, $S_3$ as data sets, a velocity sorter 19 for determining the nominal velocities $v_1$, $v_2$, $v_3$ of the sample components associated with each of the signal peaks $SP_1$, $SP_2$, $SP_3$ of each of the signals $S_1$, $S_2$, $S_3$ and grouping those signal peaks $SP_1$, $SP_2$, $SP_3$ into sets according to nominal velocity, an equiphase space-time map generator 20 for generating an equiphase space-time map of equiphase points from the signal peaks $SP_1$, $SP_2$, $SP_3$ of the signals $S_1$, $S_2$, $S_3$, and a vertex finder 22 for identifying the vertices of the equiphase points of the grouped sets of signal peaks $SP_1$, $SP_2$, $SP_3$. In this embodiment the velocity sorter 19 is provided so as to be operable prior to the equiphase space-time map generator 20. In alternative embodiments the velocity sorter 19 could be provided so as to be operable after the space-time map generator 20 or the vertex finder 22.

Figure 3:
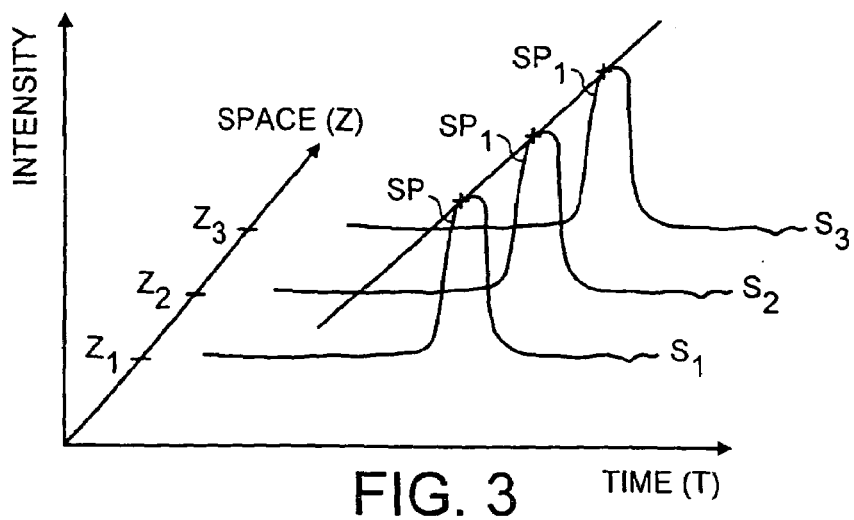
FIG. 3 illustrates a three-dimensional representation of the intensity-time signals of one component of a sample plug as detected at positions $z_1$, $z_2$, $z_3$ spaced along the separation channel of the apparatus of FIG. 1.
Figure 4:
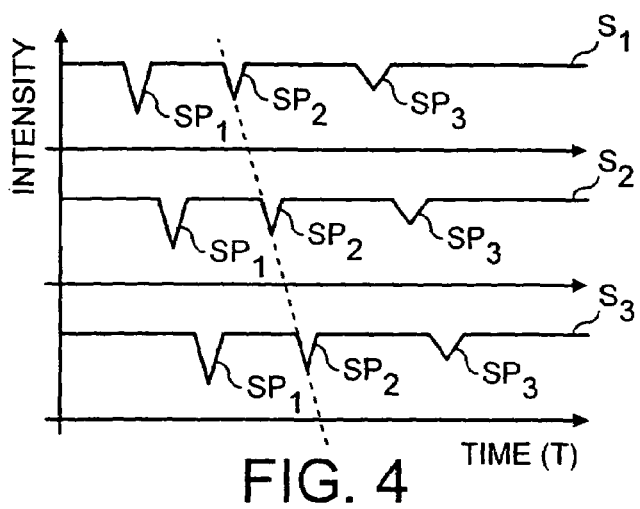
FIG. 4 illustrates the intensity-time signals of three components of a sample plug as detected at positions $z_1$, $z_2$, $z_3$ spaced along the separation channel of the apparatus of FIG. 1.

FIG. 3 is included for the purposes of illustration only and illustrates the signals $S_1$, $S_2$, $S_3$ as including only a single peak $SP_1$ from a single component of a single sample plug. In reality, however, the signals $S_1$, $S_2$, $S_3$ each include a plurality of signal peaks $SP_{1-n}$, $SP_{1-n}$, $SP_{1-n}$. FIG. 4 illustrates the signals $S_1$, $S_2$, $S_3$ as including three signal peaks $SP_1$, $SP_2$, $SP_3$ from three components of a single sample plug.

The velocity sorter 19 is configured to determine the nominal velocities $v_1$, $v_2$, $v_3$ of the sample components associated with each of the signal peaks $SP_1$, $SP_2$, $SP_3$ in each of the signals $S_1$, $S_2$, $S_3$ and then group those signal peaks $SP_1$, $SP_2$, $SP_3$ into sets according to nominal velocity. The nominal velocities $v_1$, $v_2$, $v_3$ can be calculated as the positions $z_1$, $z_2$, $z_3$ of the detector elements are fixed and the elapsed time t is extractable from the signals $S_1$, $S_2$, $S_3$, where the nominal velocities can be expressed as $v_{1-n} = z_{1-n}/t$. By grouping the signal peaks $SP_1$, $SP_2$, $SP_3$ into sets according to nominal velocity, and hence sample component, subsequent analysis is facilitated as the data points associated with each sample component can be fitted without requiring the use of complex data extraction techniques. Velocity sorting is encompassed by our earlier WO-96/35946, the content of which is incorporated herein by reference.

Figure 5:
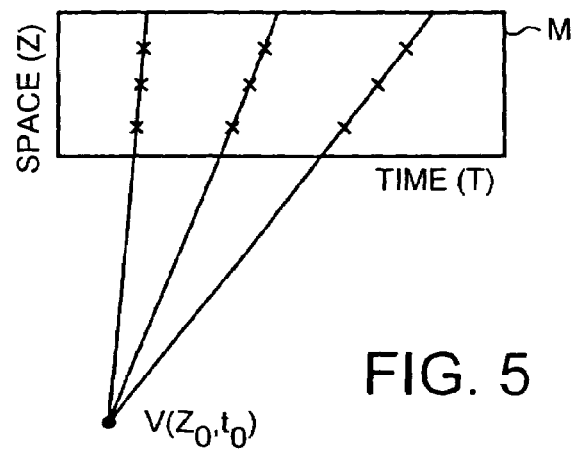
FIG. 5 illustrates a space-time map as generated from the intensity-time signals of FIG. 4.

The equiphase space-time map generator 20 is configured to determine the local minima of the signal peaks $SP_1$, $SP_2$, $SP_3$ in the signals $S_1$, $S_2$, $S_3$ detected at the detection positions $z_1$, $z_2$, $z_3$ and generate an equiphase map M in space-time dimensions from the determined local minima. FIG. 5 illustrates the space-time map M generated from the local minima extracted from the signal peaks $SP_1$, $SP_2$, $SP_3$ of the signals $S_1$, $S_2$, $S_3$.

In this embodiment each electropherogram is transformed into a set of local slopes, where a triangular slope sequence defines a signal and the local extreme is the minimum absolute local derivative.

Also, in this embodiment the time component of the detected signals $S_1$, $S_2$, $S_3$ is corrected as a function of the integrated electric current variation. Owing to the variation of various factors in electrophoretic detection, the temperature being one of the most significant, the characteristics of the separation medium, in this embodiment a gel, are altered. Firstly, the resistivity of the gel changes, leading to variations in the potential difference between the electrodes and a given point in the gel and fluctuations in the electric current. Secondly, the sieving properties of the gel change, affecting the mobility of the electrophoresed components. By monitoring the electric current, the time component of the space-time map M can be corrected as set out hereinbelow. Specifically, the time component is curved as a function of the integrated electric current variation.

The velocity of a sample component is:

$$v = dz/dt \tag{1}$$

For a transformation of the measured time component to a corrected time component $t \rightarrow t_c$, it follows that $dt \rightarrow dt_c$ and $v \rightarrow v_c$. Thus:

$$v_c/v = dt/dt_c \tag{2}$$

The transformation $v \rightarrow v_c$ can be defined as:

$$v_c/v = I(t)/I_0 \tag{3}$$

where I is the measured current and $I_0$ is the reference current which corresponds to the frame where all velocities and time components are projected.

From equations (2) and (3), it follows:

$$dt_c = I_0/I(t)dt \rightarrow t_c = \int I_0/I(t')dt' \text{ for } 0 \text{ to } t \tag{4}$$

The justification for the velocity transformation (3) is that the velocity is approximately proportional to the applied electric field, which in turn is proportional to the electric current in the separation channel 4. This correction factor has been found to work well for small current changes, with the integral of equation (4) providing for an accurate time transformation.

The vertex finder 22 is configured, in this embodiment by the use of rotational matrices, to identify the vertices V of the equiphase points of the grouped sets of signal peaks $SP_1$, $SP_2$, $SP_3$ as determined by the equiphase space-time map generator 20, where the components of each injected sample plug have a common vertex V by virtue of being time and/or spatially separated in the space-time dimension. All of the sample components injected in a single sample plug are uniquely identified by a single vertex V in space-time coordinates, thus allowing for the identification of the sample components from each of a plurality of separately-provided sample plugs. FIG. 5 illustrates the vertex V as determined from the generated space-time map M. This space-time map includes only a single vertex V as all of the components were provided in a single sample plug.

By using each vertex V as a constraint to extract the velocity spectrum of the sample components, the resolution is approximately proportional to $\sqrt{n}$, where n is the number of components. In this way, the velocity of one component is calculated using the velocities of all of the other components from the same sample plug, and thus, as the number of components in a sample increases, the resolution of the analysis increases accordingly. Such space parameterisation which results in multiple vertex formation in the form of intensity enhanced regions in space-time co-ordinates is particularly suited to the cases of multiple sample injections and multiple column correlation. The power of this technique has been demonstrated on DNA samples which include large numbers of fragments (>100) having lengths of one base pair difference, thereby providing a sequencing technique having a greatly extended dynamic range.

Figure 6:
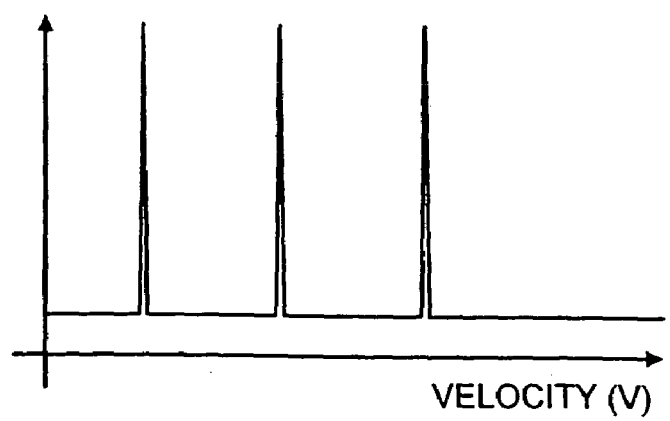
FIG. 6 illustrates the velocity spectrum as determined from the vertexed space-time map of FIG. 5.
Figure 7:
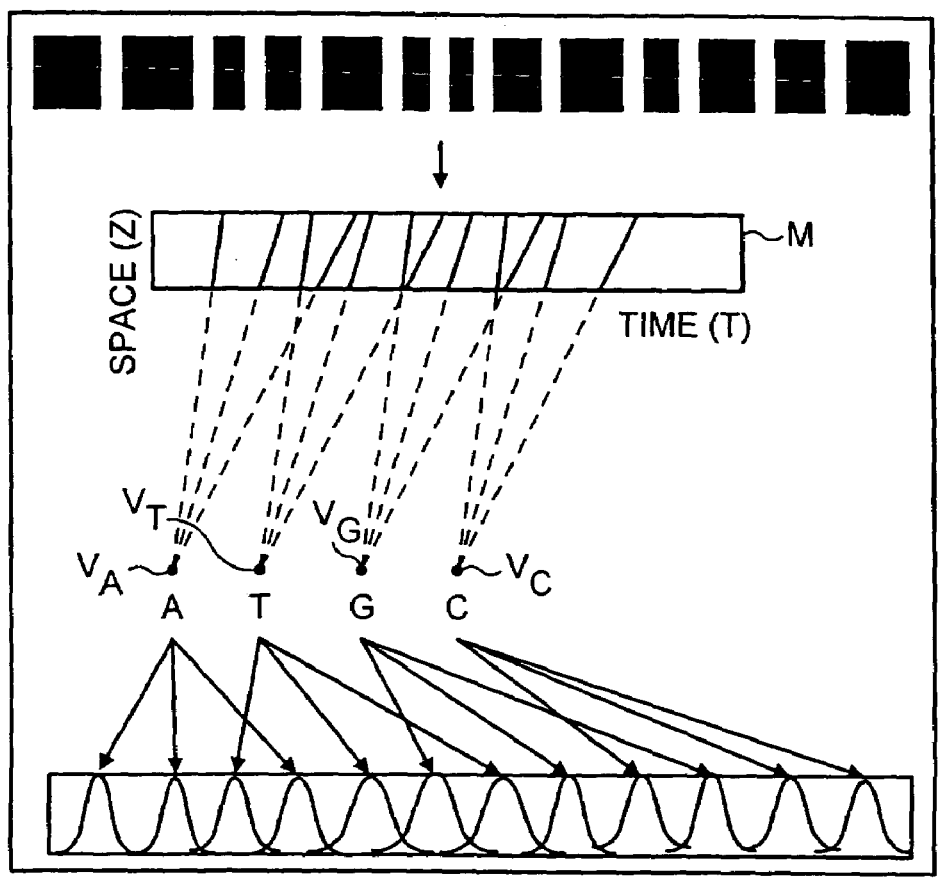
FIG. 7 illustrates a space-time map as generated from the intensity-time signals from four separately-injected DNA sample plugs comprising DNA bands having different base pair terminations.

From the determination of the vertices V in the space-time map M, high resolution of the electrophoresis data is achieved, allowing accurate determination of the velocities of the sample components as illustrated in FIG. 6.

Use of the above-described electrophoresis apparatus to sequence DNA samples having the base pair terminations A, T, G and C will now be described hereinbelow.

In use, four sample plugs comprising DNA bands having different length and one of the base pair terminations A, T, G and C are separately introduced into the ports 6, 8, 10, 12 of the separation channel 4, and electrophoretically driven therealong. In one mode of use, the sample plugs are introduced simultaneously into the ports 6, 8, 10, 12 which are spatially separated along the separation channel 4. In another mode of use, the sample plugs are introduced sequentially into one of the ports 6, 8, 10, 12 so as to be time spaced. The signals $S_1$, $S_2$, $S_3$, ..., $S_n$ detected by the detector 16 as the DNA bands pass the detecting elements at the detecting positions $z_1$, $z_2$, $z_3$, ..., $z_n$ are collected by the data collector 18. The velocity sorter 19 then determines the nominal velocities $v_1$, $v_2$, $v_3$, ..., $v_n$ of the sample components associated with each of the signal peaks $SP_1$, $SP_2$, $SP_3$, ..., $SP_n$ of the signals $S_1$, $S_2$, $S_3$, ..., $S_n$ and groups those signal peaks $SP_1$, $SP_2$, $SP_3$, ..., $SP_n$ into sets according to nominal velocity. The equiphase space-time map generator 20 then determines the local minima of the signal peaks $SP_1$, $SP_2$, $SP_3$, ..., $SP_n$ of the signals $S_1$, $S_2$, $S_3$, ..., $S_n$, and generates an equiphase space-time map M. The vertex finder 22 then identifies the vertices $V_A$, $V_T$, $V_G$, $V_C$ of the determined local minima for each of the grouped sets of signal peaks $SP_1$, $SP_2$, $SP_3$, ..., $SP_n$. In this embodiment the space-time map M includes four vertices $V_A$, $V_T$, $V_G$, $V_C$ as four sample plugs were separately injected into the separation channel 4, each being attributable to DNA bands having one of the base pair terminations A, T, G and C. In this way, the DNA sample can be sequenced, with the lengths of the DNA bands being determined from the migration velocities.

Finally, it will be understood that the present invention has been described in its preferred embodiment and can be modified in many different ways without departing from the scope of the invention as defined by the appended claims.

The invention claimed is:

1. An analysis system for enabling determination of the velocities of migrating objects, comprising:
    a space-time map generator for generating a space-time map of points representative of the signal peaks of signals detected at a plurality of spaced positions; and a vertex finder for identifying at least one vertex from the space-time map, with a single vertex being identified for each group of objects having a common constraint and the velocities of the objects being determinable from the sets of points in the space-time map corresponding to the respective objects as fitted to the respective vertex; and
    a velocity sorter for determining the nominal velocities associated with the signal peaks in the signals and grouping those signal peaks into sets according to nominal velocity.

2. The system of claim 1, wherein the space-time map generator is configured to utilize a corrected time component in generating the space-time map according to a function of the electric current variation.

3. The system of claim 1, wherein the space-time map generator is an equiphase space-time map generator for generating an equiphase space-time map of equiphase points.

4. The system of claim 3, wherein the equiphase space-time map generator is configured to transform each data set into a set of local slopes of the signals detected at a plurality of spaced positions and determine the local extrema as the minimum absolute local derivatives.

5. The system of claim 1, wherein the objects are non-labeled objects.

6. The system of claim 1, wherein the objects are labeled objects.

7. The system of claim 1, wherein the objects are migrated through a channel.

8. The system of claim 7, wherein the channel comprises a separation channel through which the objects are electrophoretically driven.

9. The system of claim 1, wherein the objects comprise components from one sample.

10. The system of claim 1, wherein the objects comprise components from a plurality of separate samples.

11. The system of claim 1, wherein the objects comprise molecular components.

12. The system of claim 1, wherein the objects comprise polymeric components.

13. The system of claim 12, wherein the components comprise DNA bands.

14. A method of enabling determination of the velocities of migrating objects, comprising the steps of:
    generating a space-time map of points representative of the signal peaks of signals detected at a plurality of spaced positions;
    identifying at least one vertex from the space-time map, with a single vertex being identified for each group of objects having a common constraint and the velocities of the objects being determinable from the sets of points in the space-time map corresponding to the respective objects as fitted to the respective vertex;

determining the nominal velocities associated with the signal peaks in the signals; and grouping those signal peaks into sets according to nominal velocity.

15. The method of claim 14, wherein a time component corrected according to a function of the electric current variation is utilized in generating the space-time map.

16. The method of claim 14, wherein the space-time map is an equiphase space-time map of equiphase points.

17. The method of claim 16, wherein the equiphase points are determined by transforming each data set into a set of local slopes and determining the local extrema as the minimum absolute local derivatives.

18. The method of claim 14, wherein the objects are non-labeled objects.

19. The method of claim 14, wherein the objects are labeled objects.

20. The method of claim 14, wherein the objects are migrated through a channel.

21. The method of claim 20, wherein the channel comprises a separation channel through which the objects are electrophoretically driven.

22. The method of claim 14, wherein the objects comprise components from one sample.

23. The method of claim 14, wherein the objects comprise components from a plurality of separate samples.

24. The method of claim 14, wherein the objects comprise molecular components.

25. The method of claim 14, wherein the objects comprise polymeric components.

26. The method of claim 25, wherein the components comprise DNA bands.

27. The method of claim 25, wherein the components comprise DNA bands.

28. The method of claim 25, wherein the components comprise DNA bands.

29. An electrophoresis apparatus including an analysis system for enabling determination of the velocities of migrating objects comprising:
a space-time map generator for generating a space-time map of points representative of the signal peaks of signals detected at a plurality of spaced positions as the objects are migrated through a separation channel through which the objects are electrophoretically driven; and
a vertex finder for identifying at least one vertex from the space-time map, with a single vertex being identified for each group of objects having a common constraint and the velocities of the objects being determinable from the sets of points in the space-time map corresponding to the respective objects as fitted to the respective vertex.

30. An analysis system for classifying migrating objects into groups each having a common constraint, comprising:
a space-time map generator for generating a space-time map of points representative of the signal peaks of signals detected at a plurality of spaced positions;
a vertex finder for identifying at least one vertex from the space-time map, with a single vertex being identified for each group of objects having a common constraint;and
a velocity sorter for determining the nominal velocities associated with the signal peaks in the signals and grouping those signal peaks into sets according to nominal velocity.

31. The system of claim 30, wherein the space-time map generator is configured to utilize a corrected time component in generating the space-time map according to a function of the electric current variation.

32. The system of claim 31, wherein the corrected time ($t_c$) is determined according to the function $t_c = \int I_0/I(t)dt$ in the range of 0 to t, where t is the measured time, I is the measured current and $I_0$ is the reference current.

33. The system of claim 30, wherein the space-time map generator is an equiphase space-time map generator for generating an equiphase space-time map of equiphase points.

34. The system of claim 33, wherein the equiphase space-time map generator is configured to transform each data set into a set of local slopes and determine the local extrema as the minimum absolute local derivatives.

35. The system of claim 30, wherein the objects are non-labeled objects.

36. The system of claim 30, wherein the objects are labeled objects.

37. The system of claim 30, wherein the objects are migrated through a channel.

38. The system of claim 37, wherein the channel comprises a separation channel through which the objects are electrophoretically driven.

39. The system of claim 30, wherein the velocities of the objects are determinable from the points in the space-time map as fitted to the respective vertex.

40. The system of claim 30, wherein the objects comprise molecular components.

41. The system of claim 30, wherein the objects comprise polymeric components.

42. A method of classifying migrating objects into groups each having a common constraint, comprising the steps of:
generating a space-time map of points representative of the signal peaks of signals detected at a plurality of spaced positions;
identifying at least one vertex from the space-time map, with a single vertex being identified for each group of objects having a common constraint;
determining the nominal velocities associated with the signal peaks in the signals; and
grouping those signal peaks into sets according to nominal velocity.

43. The method of claim 42, wherein a time component corrected according to a function of the electric current variation is utilized in generating the space-time map.

44. The method of claim 42, wherein the space-time map is an equiphase space-time map of equiphase points.

45. The method of claim 44, wherein the equiphase points are determined by transforming each data set into a set of local slopes of the signals detected at a plurality of spaced positions and determining the local extrema as the minimum absolute local derivatives.

46. The method of claim 42, wherein the objects are non-labeled objects.

47. The method of claim 42, wherein the objects are labeled objects.

48. The method of claim 42, wherein the objects are migrated through a channel.

49. The method of claim 48, wherein the channel comprises a separation channel through which the objects are electrophoretically driven.

50. The method of claim 42, wherein the velocities of the objects are determinable from the points in the space-time map as fitted to the respective vertex.

51. The method of claim 42, wherein the objects comprise molecular components.

52. The method of claim 42, wherein the objects comprise polymeric components.

* * * * *